United States Patent
Vartiovaara

(10) Patent No.: US 11,771,319 B2
(45) Date of Patent: Oct. 3, 2023

(54) INTERFACE FOR TWO-PART WEARABLE PATIENT MONITORING DEVICE

(71) Applicant: General Electric Company, Schenectady, NY (US)

(72) Inventor: Ville Petteri Vartiovaara, Helsinki (FI)

(73) Assignee: General Electric Company, Schenectady, NY (US)

( * ) Notice: Subject to any disclaimer, the term of this patent is extended or adjusted under 35 U.S.C. 154(b) by 1036 days.

(21) Appl. No.: 16/590,840

(22) Filed: Oct. 2, 2019

(65) Prior Publication Data

US 2020/0029813 A1 Jan. 30, 2020

Related U.S. Application Data

(63) Continuation of application No. 15/153,979, filed on May 13, 2016, now Pat. No. 10,463,253.

(51) Int. Cl.
*A61B 5/00* (2006.01)
*A61B 5/332* (2021.01)
(Continued)

(52) U.S. Cl.
CPC ............ *A61B 5/0017* (2013.01); *A61B 5/01* (2013.01); *A61B 5/021* (2013.01);
(Continued)

(58) Field of Classification Search
CPC ..... A61B 5/0017; A61B 5/01; A61B 5/02055; A61B 5/021; A61B 5/14542; A61B 5/318;
(Continued)

(56) References Cited

U.S. PATENT DOCUMENTS 5,721,496 A * 2/1998 Farnworth ........... G01R 1/0483
324/750.05
5,781,024 A * 7/1998 Blomberg .......... G01R 31/2829
204/406

(Continued)

FOREIGN PATENT DOCUMENTS

EP 1359842 5/2009
EP 2559280 2/2013
(Continued)

OTHER PUBLICATIONS

Radius-7 brochure, MASIMO, admitted prior art, 2014.
(Continued)

*Primary Examiner* — Jacqueline Cheng
*Assistant Examiner* — Tho Q Tran
(74) *Attorney, Agent, or Firm* — ANDRUS INTELLECTUAL PROPERTY LAW, LLP

(57) ABSTRACT

A two part patient monitoring device includes an activator module and a sensor device. The activator module includes a non-galvanic data port that creates a communication path with a non-galvanic data port on the sensor device. The activator module includes power contact pads that are each at least partially surrounded by a bias ring. A bias voltage is applied to the bias rings and a processor or circuit in the activator module monitors the voltage on the bias ring to detect a leakage current. The sensor module includes power contact pins that engage the power contact pads to transfer power from the activator module to the sensor device. Each of the contact pins are surrounded by a seal member such that the connection between the power contact pins and the power contact pads is protected from debris and/or moisture.

20 Claims, 11 Drawing Sheets

(51) Int. Cl.
  *A61B 5/145* (2006.01)
  *A61B 5/01* (2006.01)
  *A61B 5/021* (2006.01)
  *A61B 5/0205* (2006.01)
  *A61B 5/318* (2021.01)
  *A61B 5/369* (2021.01)
  *A61B 5/024* (2006.01)

(52) U.S. Cl.
  CPC ...... *A61B 5/02055* (2013.01); *A61B 5/14542* (2013.01); *A61B 5/318* (2021.01); *A61B 5/369* (2021.01); *A61B 5/7225* (2013.01); *A61B 5/02416* (2013.01); *A61B 5/332* (2021.01); *A61B 2560/0214* (2013.01); *A61B 2560/045* (2013.01); *A61B 2562/08* (2013.01)

(58) Field of Classification Search
  CPC ... A61B 5/369; A61B 5/7225; A61B 5/02416; A61B 5/332; A61B 2560/0214; A61B 2560/045; A61B 2562/08; A61B 2560/0443; A61B 2560/0456; A61B 2560/0462; A61B 2560/0468; H02H 1/003
  See application file for complete search history.

(56) References Cited

U.S. PATENT DOCUMENTS

| | | |
|---|---|---|
| 6,198,394 B1 | 3/2001 | Jacobsen et al. |
| 6,298,255 B1 * | 10/2001 | Cordero ............. A61B 5/303 600/372 |
| 6,749,566 B2 | 6/2004 | Russ |
| 7,390,299 B2 | 6/2008 | Weiner et al. |
| 8,475,368 B2 | 7/2013 | Tran et al. |
| 2004/0130446 A1 | 7/2004 | Chen et al. |
| 2004/0199056 A1 | 10/2004 | Husemann et al. |
| 2006/0094936 A1 | 5/2006 | Russ |
| 2006/0122466 A1 | 6/2006 | Nguyen-Dobinsky et al. |
| 2006/0245131 A1 * | 11/2006 | Ramey ............. H02H 7/18 361/90 |
| 2006/0282021 A1 | 12/2006 | DeVaul et al. |
| 2007/0027367 A1 | 2/2007 | Oliver et al. |
| 2007/0123783 A1 | 5/2007 | Chang |
| 2007/0179734 A1 | 8/2007 | Chmiel et al. |
| 2007/0287994 A1 | 12/2007 | Patel |
| 2008/0048667 A1 | 2/2008 | Yu et al. |
| 2008/0215360 A1 | 9/2008 | Dicks et al. |
| 2008/0281168 A1 | 11/2008 | Gibson et al. |
| 2009/0312638 A1 | 12/2009 | Bartlett |
| 2009/0318818 A1 | 12/2009 | Whitaker et al. |
| 2010/0168605 A1 | 7/2010 | Aarts |
| 2010/0249540 A1 | 9/2010 | Lisogurski |
| 2011/0021930 A1 | 1/2011 | Mazzeo et al. |
| 2011/0145894 A1 | 6/2011 | Morchon et al. |
| 2011/0152632 A1 | 6/2011 | Le Neel et al. |
| 2011/0184255 A1 | 7/2011 | Ogino et al. |
| 2012/0108917 A1 | 5/2012 | Libbus et al. |
| 2013/0017791 A1 | 1/2013 | Wang et al. |
| 2013/0109927 A1 | 5/2013 | Menzel |
| 2013/0337842 A1 | 12/2013 | Wang et al. |
| 2015/0150505 A1 | 6/2015 | Kaskoun et al. |
| 2015/0173673 A1 | 6/2015 | Toth et al. |
| 2016/0183836 A1 | 6/2016 | Muuranto et al. |

FOREIGN PATENT DOCUMENTS

| | | |
|---|---|---|
| EP | 1881784 | 10/2013 |
| WO | 2014027273 | 2/2014 |

OTHER PUBLICATIONS

IntelliVue Cableless Measurement brochure, Philips, Jun. 2013.
International Search Report and Written Opinion for International Application No. PCT/US2015/050698 dated Dec. 9, 2015.

* cited by examiner

INTERFACE FOR TWO-PART WEARABLE PATIENT MONITORING DEVICE

CROSS REFERENCE TO RELATED APPLICATION

The present application is continuation application of and claims priority to U.S. patent Ser. No. 15/153,979, filed May 13, 2016, the disclosure of which is incorporated herein by reference.

BACKGROUND

The present disclosure relates generally to medical devices and, more specifically, to medical monitoring devices for monitoring a patient's physiology and health status.

In the field of medicine, physicians often desire to monitor multiple physiological characteristics of their patients. Oftentimes, patient monitoring involves the use of several separate monitoring devices simultaneously, such as a pulse oximeter, a blood pressure monitor, a heart monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to the monitor, resulting in multiple wires running across the patient's body. Thus, currently available patient monitoring devices often inhibit patient movement, requiring a patient to stay in one location or to transport a large monitor with them when they move from one place to another. Further, currently available monitoring devices are often power intensive and either require being plugged in to a wall outlet or require replacing and recharging the device battery every few hours.

SUMMARY

The present disclosure relates to a two part patient monitoring device that includes an activator module having at least one power contact pad, a non-galvanic data port and an internal battery. The monitoring device further includes a sensor device that physically connects to the activator module such that power and data can be transferred there between. The sensor device includes at least one sensor, at least one power contact pin and a second non-galvanic data port. When the sensor device is connected to the activator module, the power contact pin engages the power contact pad to transfer power between the components. At the same time, the non-galvanic data ports allow data to be transferred between the components without a galvanic connection.

In one embodiment of the disclosure, a seal member surrounds the connection between the power contact pad and the power contact pin to restrict access to the power connection. In another contemplated embodiment, a bias ring at least partially surrounds the power contact pad. The bias ring receives a bias voltage and the bias voltage is monitored by a processor contained in the activator module. By monitoring the bias voltage, the processor is able to detect a leakage current at the power connection between the activator module and the sensor device.

In another embodiment of a wireless patient monitor comprises an activator module having a connection port that connects with any one of multiple sensor devices, a battery, and a radio transmitter wirelessly connected to a host device. The activator module connects to any one of multiple sensor devices via the connection port to provide power from the battery to the sensor device and to receive digital physiological data from the sensor device. The radio transmitter transmits the digital physiological data received from the sensor device to a host device.

Another embodiment of a patient monitoring system comprises a first sensor device having a first set of one or more detectors to collect a first physiological information from a patient, a first analog-to-digital converter to convert the first physiological information to a first digital physiological data, and a first connector configured to transmit the first digital physiological data and to receive power to power the first sensor device. A second sensor device has a second set of one or more detectors to collect second physiological information from the patient, a second analog-to-digital converter to convert the second physiological information to a second digital physiological data, and a second connector configured to transmit the second digital physiological data and to receive power to power the second sensor device. The system further includes an activator module capable of alternately connecting with the first sensor device and the second sensor device. The activator has a battery, a connection port configured to connect with the first connector and the second connector to provide power from the battery to the first sensor device and the second sensor device and to receive digital physiological data from the first sensor device and the second sensor device, and a radio transmitter configured to transmit the first digital physiological data and the second digital physiological data to a host device.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
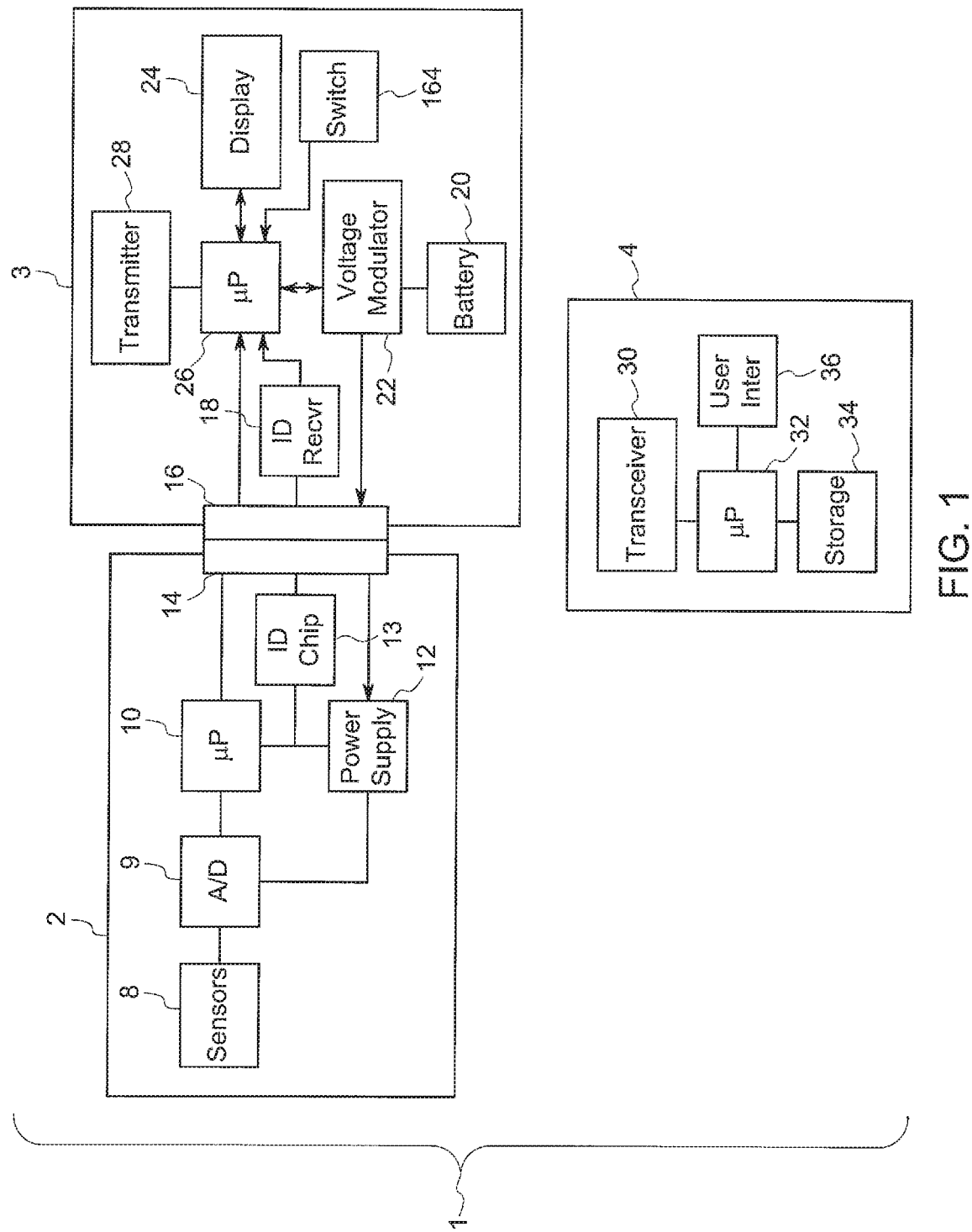
FIG. 1 is a block diagram of one embodiment of a wireless patient monitoring system including a sensor device, a generic activator device, and a host device.
Figure 2:
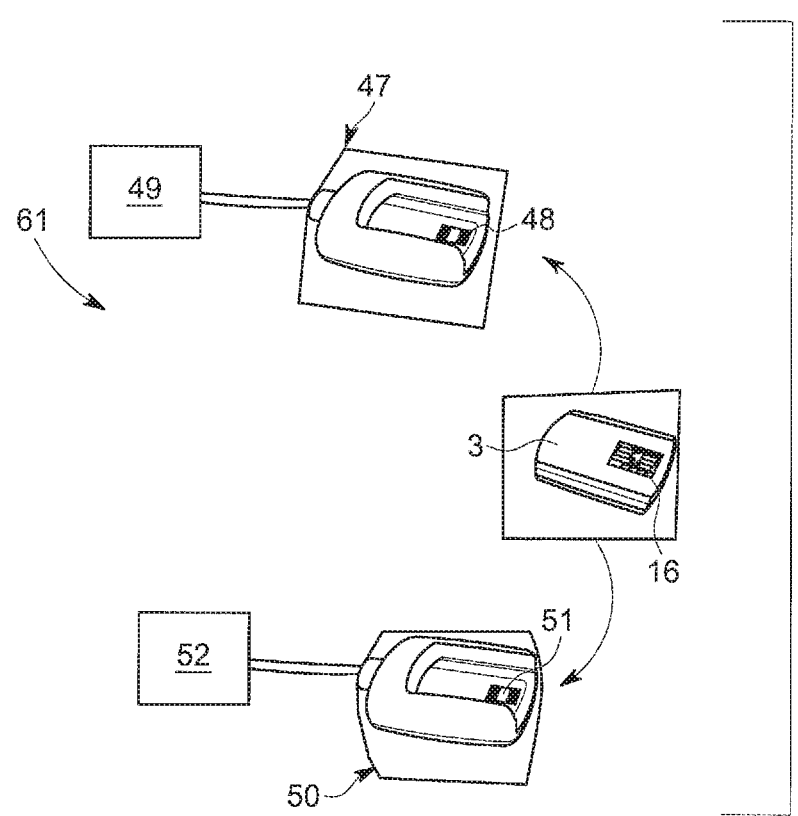
FIG. 2 depicts one embodiment of a wireless patient monitor including a first sensor device, a second sensor device, and a generic activator module.

FIG. 1 depicts one embodiment of a wireless patient monitoring system 1 including a sensor device 2, a generic activator module 3 and a host device 4. FIG. 2 depicts one embodiment of a wireless patient monitoring system demonstrating the interaction between one or more sensor devices and the generic activator module 3. The generic activator module 3 is connectable with any one of several different types of sensor devices 2 to provide power to the sensor device 2 and to transmit the digital physiological data produced by the sensor device 2 to a host device 4. A monitoring system, such as that shown in FIG. 2, may further include any number of generic activator modules 3 that are interchangeable with one another and are each configured to pair with any of the available types of sensor devices. The generic activator modules 3 may be rechargeable, such as by containing rechargeable batteries, and may be interchanged in order to maintain power to any sensor device 2.

For example, the generic activator module 3 demonstrated in FIG. 2 is connectable to any one of a number of different sensor devices 2 such as the first sensor device 47 and the second sensor device 50. The first sensor device 47 has a first set of patient sensors 49, and the second sensor device 50 has a second set of patient sensors 52. The first sensor device 47 and the second sensor device 50 may be any devices for sensing patient physiological data. For example, the first sensor device 47 may be an ECG sensor device wherein the first patient sensors 49 are ECG leads, and the second sensor device 50 may be an EEG sensor device wherein the second patient sensors 52 are EEG leads. The generic activator module 3 of FIG. 2 may be inserted into or otherwise connected with either of the first sensor device 47 or the second sensor device 50 to activate that device 47 or 50 and transmit the data collected by that device to the host device. Such connection is made by positioning generic activator module 3 so that the universal connection port 16 of the generic activator module 3 is in contact with the connector 48 of the first sensor device 47 or the connector 51 of the second sensor device 50. It should be understood that contact between the generic activator module 3 and the first or second sensor devices 47, 50 may be an electrical contact or any other connection that allows communication and power transfer. In alternative embodiments, the connection may be through means not requiring galvanic contact between the generic activator module 3 and the first or second sensor devices 47, 50. For example, the generic activator module 3 may be connected to the first or second sensor devices 47, 50 via an optical data transfer and a capacitive power transfer. Additionally, the generic activator module 3 may be configured to process the physiological data from the various sensor devices, such as the EEG data or ECG data in the present example, and/or to display physiological information about the patient derived from the physiological data.

Returning to FIG. 1, the depicted embodiment has a sensor device 2 with one or more patient sensors or detectors 8 connected to a processor 10. The one or more patient detectors 8 may include any sensors, leads, or other devices available in the art for sensing or detecting physiological information from a patient, which may include but are not limited to electrodes, lead wires, or available physiological measurement devices such as blood pressure cuffs, pulse oximetry sensors, temperature sensors, etc. The physiological signals recorded by the patient detectors 8 are digitized by analog-to-digital converter (A/D converter) 9. The A/D converter 9 may be any device or logic set capable of digitizing analog physiological signals. For example, the A/D converter 9 may be an Analog Front End (AFE). Processor 10 receives the digital physiological data from the A/D converter 9 and may transmit the processed data and the raw digitized physiological data to the generic activator module 3 via the connector 14.

The processor 10 may be configured to perform various functions depending on the type of sensor device 2 detected. For example, if the sensor device 2 is a noninvasive blood pressure (NIBP) monitor then the processor may be configured to process the physiological data detected by the sensors in a blood pressure cuff to calculate systolic, diastolic and mean blood pressure values. Likewise, the processor 10 may also be configured to determine a heart rate when the generic activator module 3 is connected to an ECG sensor device. Likewise, the processor 10 may be configured to determine a blood oxygenation value for the patient when the generic activator module 3 is connected to a sensor device 2 that is a pulse oximeter sensor device. Likewise, the processor 10 may be configured to also detect when it is connected to an electroencephalograph (EEG) sensor device and then determine a depth of anesthesia measurement value, such as an entropy value or a sedation responsiveness index value. In an embodiment where the sensor device 2 is a thermometer or temperature sensor device, the processor 10 may be configured to determine a temperature for the patient, such as a mean temperature. Alternatively or additionally, the processor 26 of the generic activator module 3 may be configured to process the digital physiological data from the sensor device 2 to calculate any or all of those aforementioned values. It should be understood that the device and system of the present disclosure is not limited to the examples provided, but may be configured and employed to monitor any clinical parameter. The examples provided herein are for the purpose of demonstrating the invention and should not be considered limiting.

In another alternative embodiment, the sensor device 2 may not contain any processor. In such an embodiment, the digitized physiological data would be sent from the A/D converter 9 of the sensor device 2 to the generic activator module 3. Accordingly, the generic activator module 3 may be configured to receive digitized raw data or digitized filtered data from various types of sensor devices 2, which is the physiological data detected by the patient detectors 8 of the various sensor devices that has been digitized by the A/D converter 9.

The processor 10 and the A/D converter 9 receive power from the power supply 12. The power supply 12 may be a simple conductor that conducts power received from the generic activator module 3 via the connector 14. Alternatively, the power supply 12 may include a battery that stores energy received from the generic activator module 3 and distributes that power to the various powered elements of the sensor device 2. Moreover, the power supply 12 may further include power management capabilities. This may be the case in embodiments where the sensor device 2 contains more demanding electromechanical aspects, such as a noninvasive blood pressure monitor. In other embodiments where the sensor device 2 has only simple components, such as an embodiment only having patient sensors 8 and an analog to digital converter 9, the power management capabilities may not be necessary and may be excluded from the sensor device 2.

The sensor device 2 has a connector 14 that is configured to connect with the universal connection port 16 on the generic activator module 3. The connector 14 and the universal connection port 16 may be configured in any manner known in the art for performing the functions described herein. The purpose of the interface is to transfer power to the sensor device 2 and data to and from the sensor device 2. Examples of methods for transferring power though the interface 14, 16 are through galvanic connectors, through inductive or capacitive coupling. Examples of methods for transferring data through the interface 14, 16 are through galvanic connectors or using optical data transfer. In one embodiment, the connector 14 and the universal connection port 16 may each be a universal asynchronous receiver/transmitter (UART), and thus may include an integrated circuit to translate data between parallel and serial forms. The universal connection port 16 and the connection port 14 may alternatively be $I^2C$ or Serial Peripheral Interface (SPI). The data communication between the sensor device 2 and the activator module 3 may alternatively be implemented using RF communication such as Bluetooth, near field communication (NFC), ANT or any other protocol suitable for short range communication. Due to the close proximity of the sensor device 2 and the activator module 3, the RF power required and the antennae can be optimized to provide very local RF communication.

In any embodiment, the universal connection port 16 is configured to receive and connect with the connectors 14 of various types of sensor devices 2. For example, the connector 14 may be configured identically for all types of sensor devices 2. In other embodiments, the connector 14 may be configured differently for various types of sensor devices 2. For example, the connector may have more or less connection points for transmitting digitized physiological data and power depending on the type of sensor device 2 and how many data channels are collected. The connection points may be electrical contact points, aligned inductive coils, aligned optical components, or any connects capable of transferring data and power between the generic activator module 3 and a sensor device. As another example, the connector 14 may provide a connection point to an identification chip or element 13 in a sensor device 2 to provide an identification pin for the sensor device 2 to the generic activator module 3. Alternatively, in other sensor devices 2 an identification pin for the sensor device 2 to the generic activator module 3 may be provided by a processor 10. The universal connection port 16 may be configured to connect with each such connector of various sensor devices.

When the connector 14 of the sensor device 2 is connected the generic activator module 3, power is provided from the generic activator module 3 to the sensor device 2, and digital physiological data is provided from the sensor device 2 to the generic activator module 3. Additionally, the sensor device 2 may identify itself to the generic activator module 3 through the connector 14 in communication with the universal connection port 16. A sensor device 2 may have an identification chip or element 13 which provides an identification pin for that sensor device 2. In the embodiment of FIG. 1, the identification device 13 of the sensor device 2 is in communication with the identification receiver 18 of the generic activator module 3. The identification receiver 18 then communicates the identification pin to the processor 26 of the generic activator module 3 such that the generic activator module 3 can identify the sensor device 2 to which it is connected. In another embodiment, the processor 10 of the sensor device 2 may directly provide an identification pin through the connector 14 and the universal port 16 to the processor 26 of the generic activator module 3. In such an embodiment, a sensor device 2 may not contain any identification device 13. However, in embodiments where the sensor device 2 does not have a processor or where the processor of a sensor device 2 does not provide an identification pin, the identification device 13 may be employed.

In the embodiment of FIG. 1, the generic activator module 3 has a processor 26 that receives digital physiological data transmitted from the sensor device 2. The processor 26 may be configured to process the digital physiological data prior to transmitting the data to the host device 4 or displaying the physiological data on the user interface display 24. In other embodiments, the processor 26 of the generic activator module 3 may not process the digital physiological data at all, as generic activator module 3 may receive digital physiological data from a sensor device 2 and relay that data to a host device 4 via a wireless connection to the host device. As described with respect to exemplary embodiments herein, the processor 26 may be configured to detect the type of sensor device 2 to which the generic activator module 3 is connected and to conduct various levels of data processing depending on the configuration of the generic activator module 3 and depending on the sensor device 2 to which the generic activator module 3 happens to be connected.

The processor 26 may also control the user interface display 24 to display physiological information about the patient. The displayed physiological information may be calculated by the processor 26 based on the digital physiological data received from the sensor device 2 or by the processor 10 in the sensor device. For example, if the sensor device 2 is an ECG sensor device 42 (FIG. 3), the processor 26 may process digital ECG data received from the ECG sensor device to calculate a heart rate, and then may display the heart rate on the user interface display 24. In an alternative embodiment, the ECG sensor device 42 may contain a processor 10 that calculates the heart rate on the digital ECG data. In such an embodiment, the processor 26 of the generic activator module may simply operate to display the heart rate calculated at the ECG sensor device 42 on the UI display 24.

The processor 26 may operate radio frequency antenna/transmitter 28 to transmit data to a host device 4, where the data may be further processed and/or stored. The radio frequency antenna/transmitter 28 of the generic activator module 3 and the RF antenna/transmitter 30 of the host device 4 may be any devices known in the art for wirelessly transmitting data between two points. In one embodiment, the RF antenna/transmitters 28 and 30 may be body area network (BAN) devices, such as medical body area network (MBAN) devices, that operate as a wireless network of wearable or portable computing devices. In such an embodiment, one or more generic activator modules 3 which may be connected to various sensor devices 2 attached to the patient may be in communication with a host device 4 positioned in proximity of the patient. Other examples of radio protocols that could be used for this purpose are Bluetooth, Bluetooth Low Energy (BLE), ANT and ZigBee.

Figure 3:
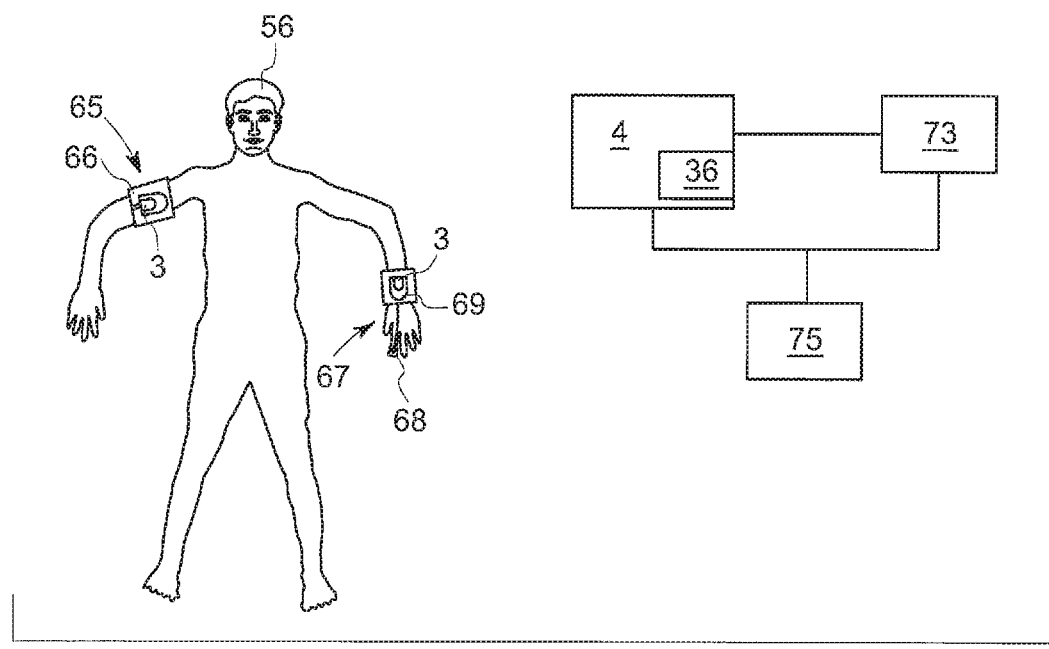
FIG. 3 depicts another embodiment of a wireless patient monitoring system configured to monitor a patient.

For example, turning to FIG. 3, a patient 56 may be monitored by two or more sensor devices 2, such as a noninvasive blood pressure sensor device 65 and a pulse oximeter sensor device 67. Each of the sensor devices 65 and 67 may be engaged with a generic activator module 3 to activate and power the sensor devices 65 and 67 and transmit the data collected by each of the sensor devices 65 and 67 to a host device 4. In an embodiment where the host device 4 is a part of a BAN, the host device 4 would be in proximity to the patient 56, such as attached to the patient's body, placed on or near the patient's bed, or positioned within range of the patient such as in the same room as the patient.

Any host device 4 may have a user interface 36 which may display data from the various sensor devices 65 and 67 on the same BAN for the patient 56. The host device 4 may further transmit the physiological data for the patient gathered by the sensor devices 65 and 67 to a central monitoring station 73 and/or to a central storage location 75. The central monitoring station 73 may provide a central location for attending clinicians to monitor patient status and/or receive alarm notifications. The central monitoring station 73 may be a local network having servers housed within a medical facility, or it may be a cloud-based system hosted by a cloud computing provider. The central storage 75 may be a central storage location for patient information to be stored long term, such as information that may become part of a patient's medical record and/or may be accessible by an attending clinician from any remote location.

In another embodiment, the host device 4 may be a remote device, such as central hub for a network of many monitoring devices within a healthcare facility or a subset of a healthcare facility. In such an embodiment, the RF receiver/transmitter 28 of the generic activator module and the RF receiver/transmitter 30 of the host device may operate on a longer-range wireless network, such as a network operating on the wireless medical telemetry service (WMTS) spectrum or on a WiFi-compliant wireless local area network (WLAN). In such an embodiment, the host device 4 may be receiving digital physiological data from two or more generic activator modules 3 connected to different patients within range of the host device 4. For example, a host device may be associated with a section of a healthcare facility, such as a unit or a floor, and may receive digital physiological data from all of the patients in that area.

The processor 26 may be further configured to operate the power gauge and protection module 22 which is connected to the battery 20. Thereby, the processor 26 and the power gauge and protection module 22 may regulate the power distribution within the generic activator module 3 and the sensor device 2. For example, the power from the battery 20 may be distributed to power the processor 26, the UI display 24 and the RF antenna/transmitter 28 in the generic activator module. The battery 20 may be any battery capable of providing sufficient power, and is preferably a rechargeable battery. Further, when the generic activator module 3 is connected to a sensor device 2, power is further distributed from the battery 20 through the power gauge and protection module 22 to the sensor device 2 through the universal connection port 16 and the connector 14. As described above, the sensor device 2 may have a power supply module 12 that distributes power within the sensor device 2. Alternatively, the power gauge and protection module 22 may distribute power directly to devices within the sensor device 2, such as to the A/D converter 9, processor 10, and/or identification device 13.

The host device 4 has receiver/transmitter 30 which is in communication with the RF receiver/transmitter 28 and the generic activator module 3. The host device may further comprise a processor 32, a user interface 36, and digital storage 34. The processor 32 may further process digital physiological data received from one or more generic activator modules 3 in communication with the host device 4. The host device may further display the patient's physiological information on the user interface 36. The user interface 36 may be utilized by a clinician to view details of the digital physiological data collected by the sensor devices 2. The user interface 36 of the host device 4 may be used by a clinician to view aspects of the digital physiological data for the patient that are not viewable on the display of the generic activator module 3. For example, in an embodiment where a sensor device 2 is an ECG sensor device 42, a clinician may not be able to review ECG waveforms recorded by the ECG sensor device 42 on the user interface 36 of the host device 4 because, in some embodiments, the user interface display 24 of the generic activator module 3 may be too small to display full waveforms, such as ECG waveforms.

The host device 4 may also have a digital storage device 34 for storing the physiological data collected by the various sensor devices 2 in communication with the host device 4 through various generic activator modules 3. The storage location 34 may also store processed physiological data created by the processor 32 of the host device, the processor 26 of the generic activator module 3, and/or the processor 10 of the sensor device 2.

The sensor devices 2 may be attached to the patient by various mechanisms so that the wireless patient monitoring devices can be worn, or maintained, on or near the patient and the patient can remain mobile and not get tangled, disconnected, or loosing monitoring. For example, as shown in FIG. 3, the noninvasive blood pressure sensor device 65 may be attached to the blood pressure cuff 66 which may be worn by the patient. Likewise, the pulse oximeter sensor device 67 may be attached to wristband 69 which may be worn by the patient. In other embodiments, various sensor devices 2 may be attached to the patient by various means which are proximate to the area where the patient detectors 8 are attached to the patient. For example, an ECG sensor device 42 (FIG. 4) may be connected to the patient via a chest strap or a waist strap. In another embodiment, an EEG sensor device may be attached to a patient by a headband, neckband, chest band, or armband, or may be attached directly to an ECG electrode or a separate accessory adhered to the skin of the patient. The generic activator module 3 would then connect to and be worn with each sensor device 2 wherever that sensor device is contained on the patient.

Figure 4:
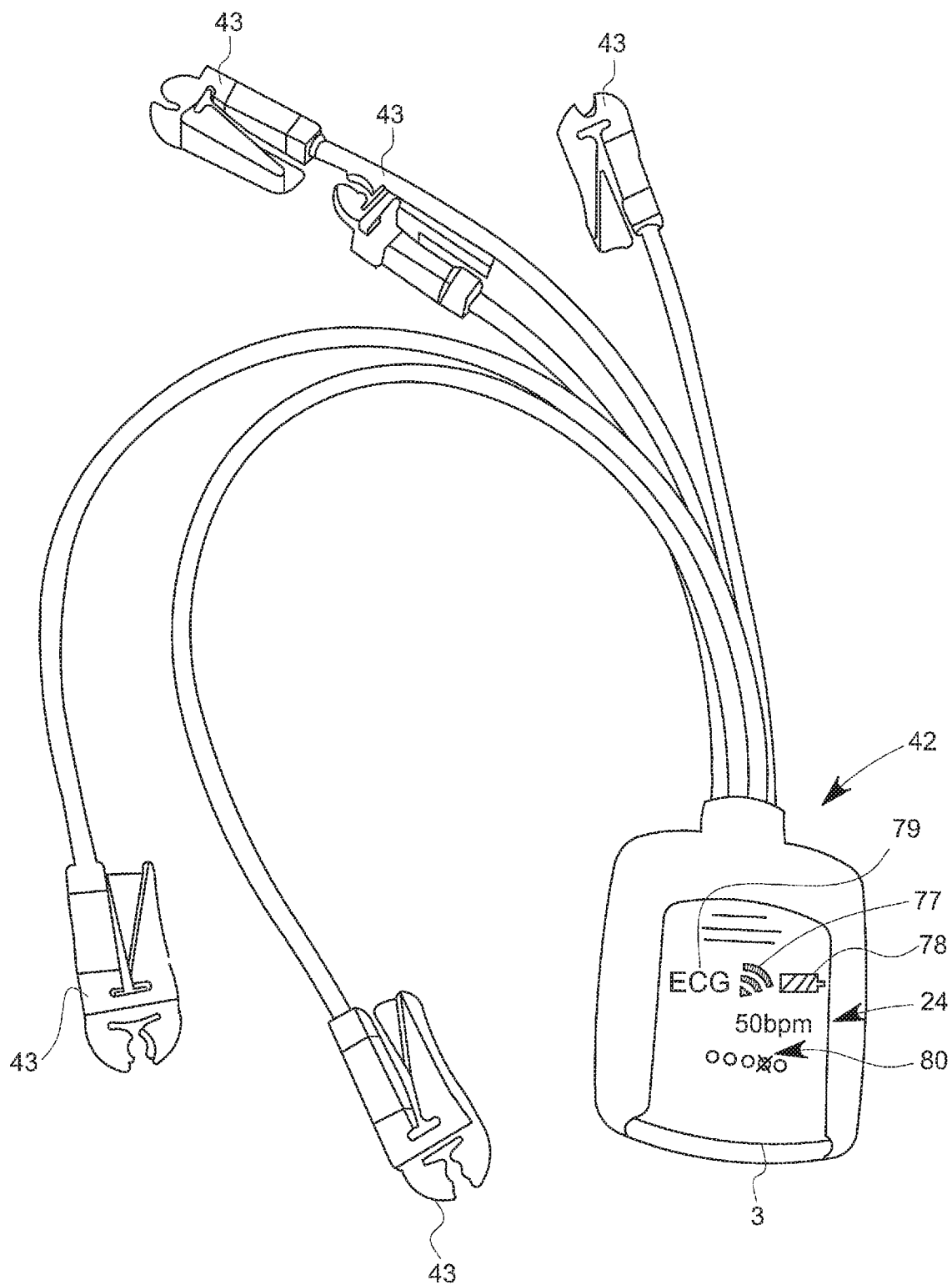
FIG. 4 depicts another embodiment of a wireless monitor including an ECG sensor device and a generic activator module.

Exemplary displays 24 for generic activator modules 3 are provided in FIGS. 4-7. FIG. 4 depicts an ECG sensor device 42 connected to a generic activator module 3. The ECG sensor device 42 has ECG detectors 43 that collect ECG data from a patient. It should be understood that the ECG detectors 42 may be any sensors, leads, or other devices capable of detecting patient cardiac signals. In the embodiment of FIG. 4, the display 24 of the generic activator module 3 displays the letters "ECG" on the connected device indicator 79 to signify that the generic activator module 3 is connected to an ECG sensor device 42.

The display 24 in FIG. 4 also displays a heart rate in beats per minute (BPM), which may be calculated by a processor in the generic activator module 3 or in the sensor device 2 based on the physiological data collected by the detectors 43. The display 24 may also provide a wireless connection status indicator 77 to indicate the status of the connection between the generic activator module 3 and the host device 4. The wireless connection status indicator 77 in FIG. 4 is a series arched lines that light up to show the wireless connection strength between the generic activator module 3 and the host device 4. However, the wireless connection status indicator 77 may take on any form capable of communicating the connectivity strength or status between the RF receiver/transmitter 28 of the generic activator module 3 and the RF receiver/transmitter 30 of the host device 4. For example, the wireless connection status indicator 77 may simply indicate the presence or absence of a wireless connection between the generic activator module 3 and the host device 4. The display 24 may also have a charge status indicator 78 to indicate the charge level of the battery in the generic activator module 3. The display 24 may also have an indicator to indicate the pairing status of the sensor (not shown), i.e. if the sensor is currently paired to a host device.

Additionally, the display unit may contain a detector status indicator 80 to indicate the status of the detectors 43 and their connectivity to the patient. In the embodiment shown in FIG. 4, the detector status indicator 80 is a series of five dots, each representing one of the detectors 43. The fourth dot is provided with an "x" through it to indicate that the sensor associated with that dot is not properly connected to the patient. This may be because the lead and/or the sensor are not properly connected to the patient, or it may be due to a failure of the detector device. In other embodiments, the detector status indicator 80 may be provided in any manner that would effectively communicate whether the detectors 43 are properly functioning and detecting physiological information from the patient. For example, the display 24 may provide a "sensor off" notification if a detector 43 is not properly connected to a patient, or it may provide a "sensor failure" notification if a detector 43 is not functioning properly.

The display 24 may also provide various other indicators. In other embodiments, the display 24 may offer a system function indicator to indicate whether the sensor device 2 and/or the generic activator module 3 are functioning properly and, if a malfunction occurs, indicate what the malfunction or problem is.

Figure 5:
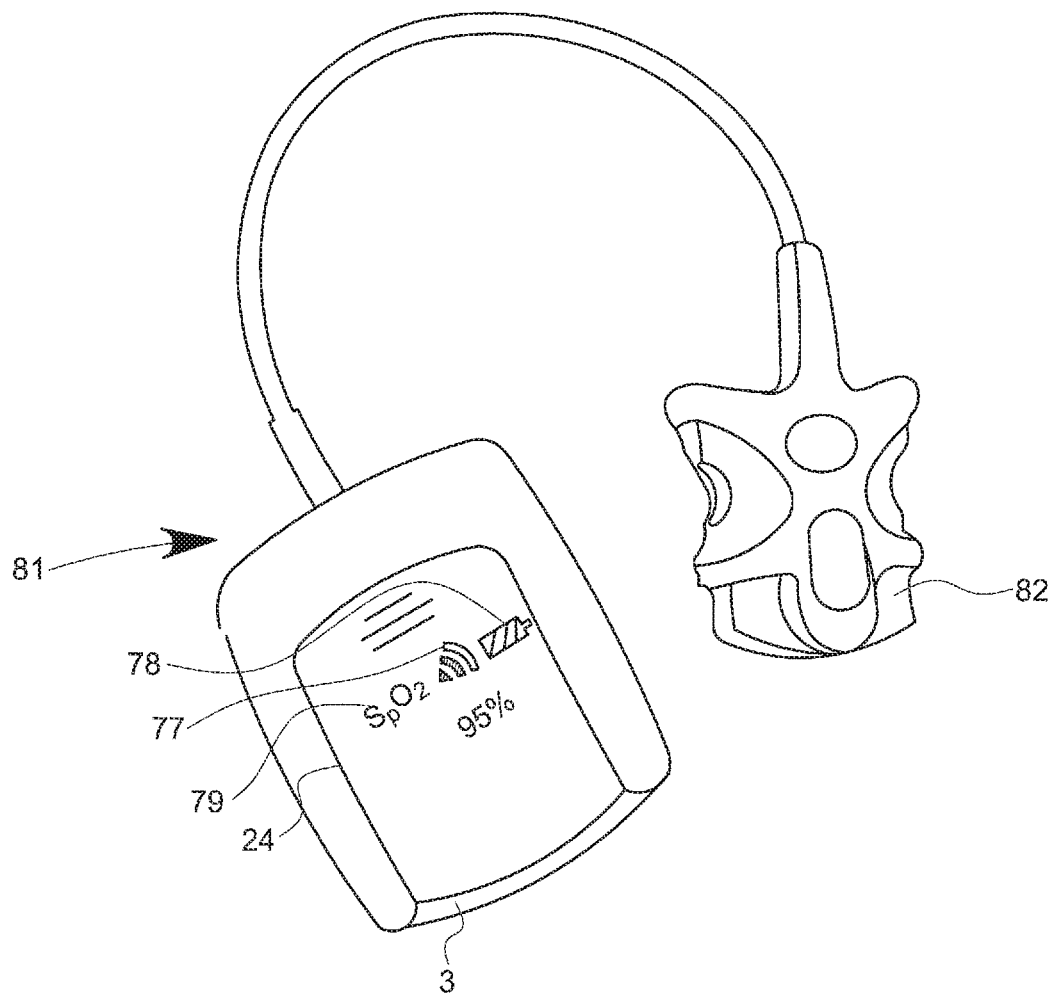
FIG. 5 depicts another embodiment of a wireless monitor including a pulse oximeter sensor device and a generic activator module.

FIG. 5 depicts a pulse oximeter sensor device 81 connected to a generic activator module 3. The pulse oximeter sensor device 81 has a pulse oximeter detector 82 that attaches to a patient, such as the patient's finger or ear, to measure blood oxygenation. In the embodiment of FIG. 5, the display 24 of the generic activator module 3 provides a connected device indicator 79 displaying "SpO$_2$" and an SpO$_2$ percentage value calculated based on the measurements taken by the pulse oximeter detector 82 connected to a patient.

Figure 6:
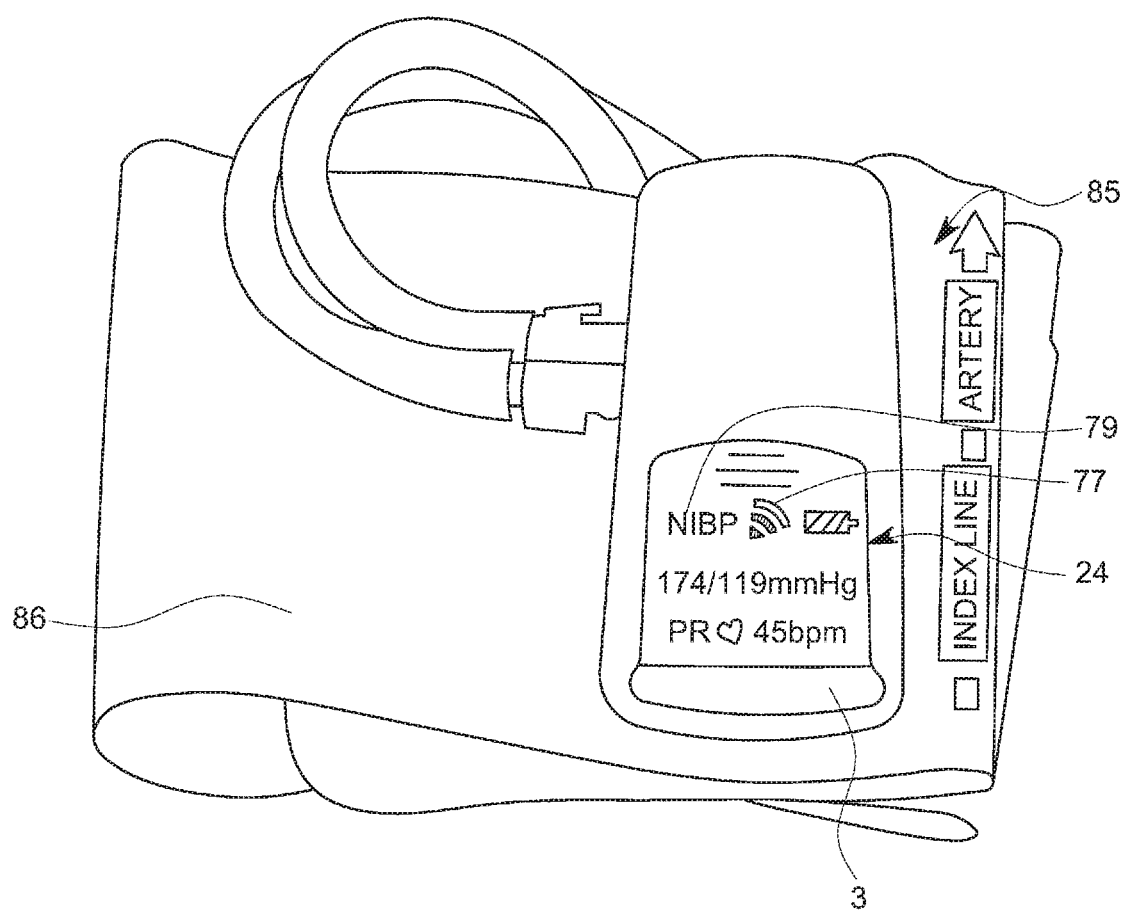
FIG. 6 depicts another embodiment of a wireless monitor including a blood pressure sensor device and a generic activator module.

FIG. 6 provides an example embodiment of a noninvasive blood pressure (NIBP) sensor device 85 paired with a generic activator module 3. The NIBP sensor device 85 has a blood pressure cuff 86 to noninvasively measure a patient's blood pressure. The information gathered by the noninvasive blood pressure cuff 86 is communicated from the NIBP sensor device 85 to the generic activator module 3 as described above. The display 24 of the generic activator module 3 provides a connected device indicator 79 displaying "NIBP" to indicate that the generic activator module 3 is paired with an NIBP sensor device 85. The display 24 also displays the blood pressure value for the patient as well as the patient's pulse rate, which are values calculated based on the blood pressure data measured by the blood pressure cuff 86.

Figure 7:
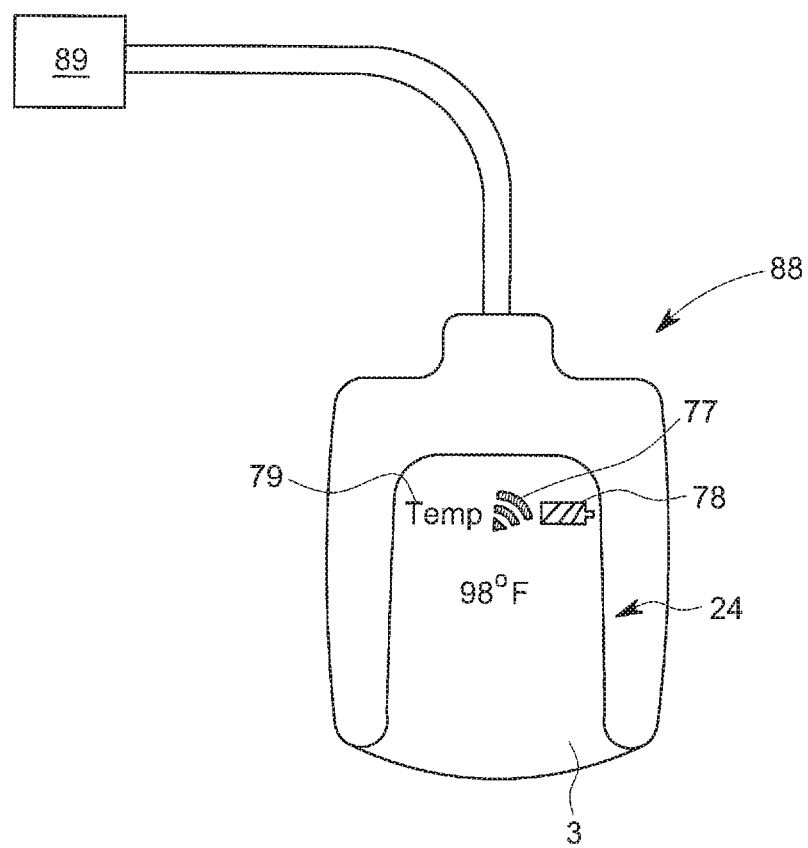
FIG. 7 depicts another embodiment of a wireless monitor including a temperature sensor device and a generic activator module.

FIG. 7 depicts an embodiment of a temperature sensor device 88 connected to a generic activator module 3. The temperature sensor device 88 has a temperature detector 89 which is attachable to a patient to measure the patient's temperature. The temperature detector 89 may be, for example, an adhesive thermometer device that adheres to a patient, such as on a patient's forehead, neck, or armpit, to measure the temperature of that location on the patient or a central temperature sensor, such as a catheter. The display 24 of the generic activator module 3 has a connected device indicator 79 displaying "temp" to indicate that the generic activator module 3 is paired with a temperature sensor device 88. Further, the display 24 of FIG. 7 is displaying a temperature measured by the temperature sensor device, which is displayed as 98° F. Likewise, the wireless connection status indicator indicates the wireless connection status of the generic activator module 3 and the charge status indicator 78 indicates the battery charge of the generic activator module 3.

Each type of sensor device 2, such as those described herein, may have varying levels of complexity. For example, the ECG sensor device 42 of FIG. 4 may contain a processor to process the ECG data collected by the detectors 43 to determine or calculate information based on the measured cardiac signals, such as heart rate and/or the presence of abnormal waveforms. In other embodiments, the ECG sensor device 42 may not contain any processor 10 and the digitized raw physiological data may be sent from the ECG sensor device 42 to the generic activator module 3 there to bear with. In such an embodiment, the generic activator module 3 may contain a processor that processes the digitized raw ECG data detected by the ECG sensor device 42. In still other embodiments, the generic activator module 3 may not process the digitized raw ECG data and may simply relay the data to the host device 4 via the RF receiver/transmitter 28 housed therein.

Certain sensor devices may be larger and more complicated and thus may necessitate having an internal processor 10 and/or an internal power supply 12 housed therein. For example, an NIBP sensor device 85 requires more significant electromechanical elements to operate the blood pressure cuff which may require power management to be internal to the NIBP sensor device 85. Thus, it may be preferable to house a processor 10 within the NIBP sensor device 85 which can process the physiological data gathered by the blood pressure cuff 86. Conversely, the temperature sensor device 88 may be a very simple device, and it may be preferable to not include a processor or power management within the temperature sensor device 88. In one embodiment, the temperature sensor device 88 may be a disposable device, and thus for cost reasons, it would be preferable to limit the amount of elements in the temperature sensor device 88 to limit the cost of the disposable device.

As discussed previously, FIG. 2 illustrates a first embodiment for the physical configuration for the activator module 3 and the sensor device 2, illustrated by the pair of sensor devices 47, 50 shown in FIG. 2. Although this physical configuration is illustrated as one exemplarily embodiment, various different physical configurations are contemplated as being within the scope of the present disclosure.

Figure 8:
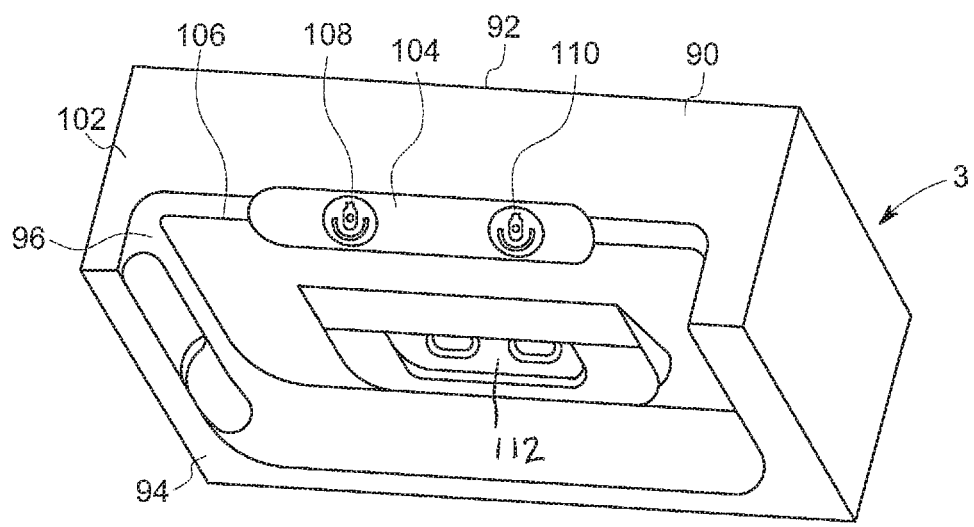
FIG. 8 is a front perspective view of one embodiment of the activator module.
Figure 9:
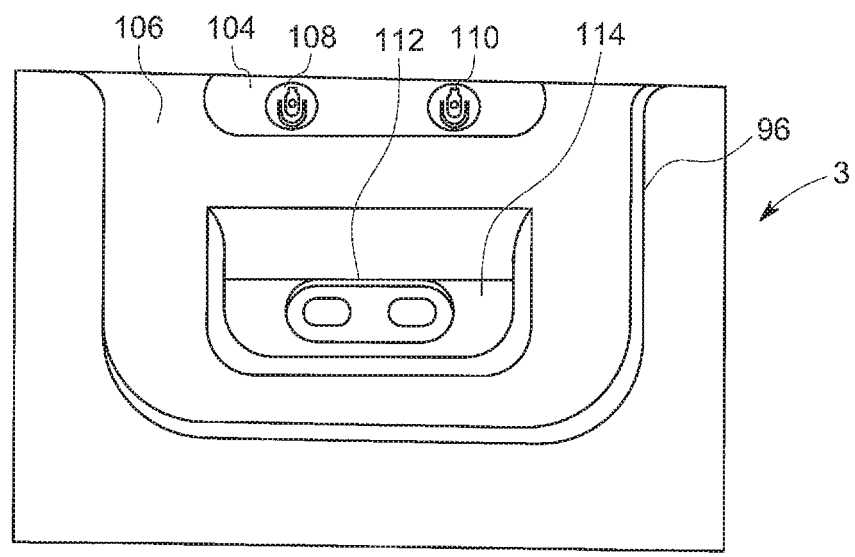
FIG. 9 is a bottom view of the activator module of FIG. 8.
Figure 10:
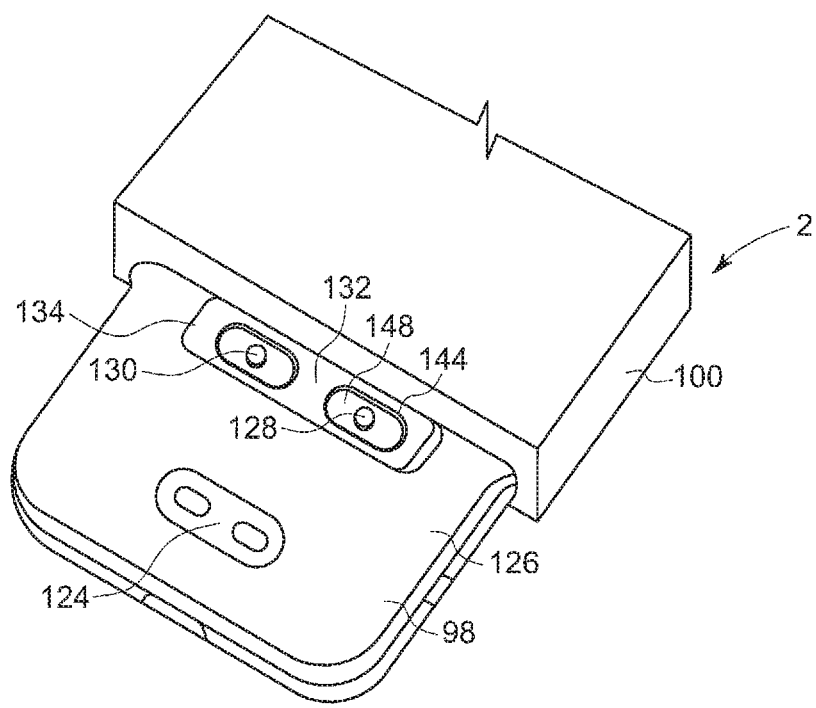
FIG. 10 is a front perspective view of one embodiment of the sensor device.
Figure 11:
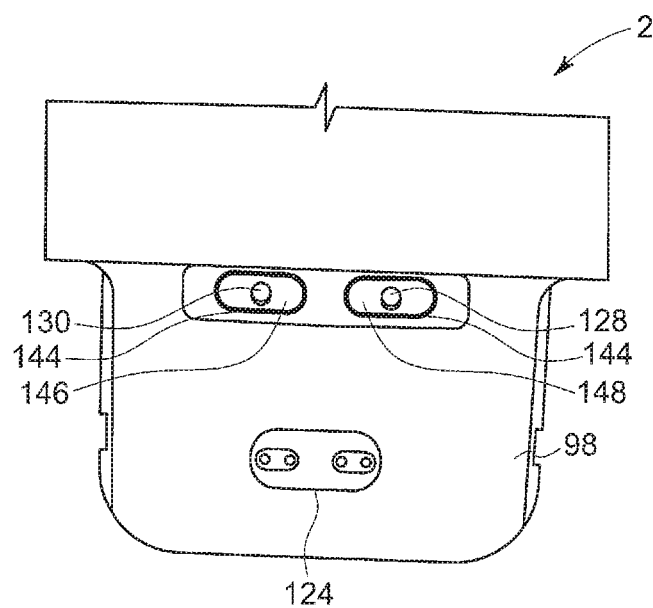
FIG. 11 is a top view of the sensor device shown in FIG. 10.

FIGS. 8 and 9 illustrate a first, alternate embodiment for the physical configuration of the activator module 3 constructed in accordance with the present disclosure. The activator module 3 shown in FIGS. 8 and 9 includes a molded outer housing 90 that includes a front surface 92 including the display 24, not shown in FIG. 8 but as illustrated in the embodiments of FIGS. 4-7. The rear surface 94 is designed including a receiving channel 96. The receiving channel 96 is recessed from the rear surface 94. The recessed receiving channel 96 is sized to receive the connecting portion 98 of the sensor device 2, which is shown in FIGS. 10 and 11. The connecting portion 98 extends from the sensor housing 100 and is sized to securely fit within the receiving channel 96. When the connecting portion 98 is received in the receiving channel 96, the sensor device 2 is able to transmit data to the activator module and receive power from the activator module as will be described in greater detail below.

Referring back to FIG. 8, the outer housing 90 includes a generally planar front face 102. A contact face surface 104 is angled relative to both the front face 102 and the base wall 106 of the receiving channel 96. The contact face surface 104 includes both a first contact pad 108 and a second contact pad 110. The first and second contact pads 108, 110 are internally connected to the battery 20 contained within the activator module, as shown in FIG. 1. The pair of contact pads 108, 110 form part of the generic connection port 16 shown in FIG. 1.

Referring back to FIGS. 8 and 9, in addition to the pair of contact pads 108, 110, the activator module 3 includes an optical data port 112 that is able to both transmit and receive data through an optical data transmission path. The optical data port 112 is formed within a generally flat face surface 114 that extends above the base wall 106 of the receiving channel 96. The optical data port 112 is sized and positioned to receive data signals from the sensor device when the sensor device is mated with the activator module 3, as will be described in detail below.

Figure 12A:
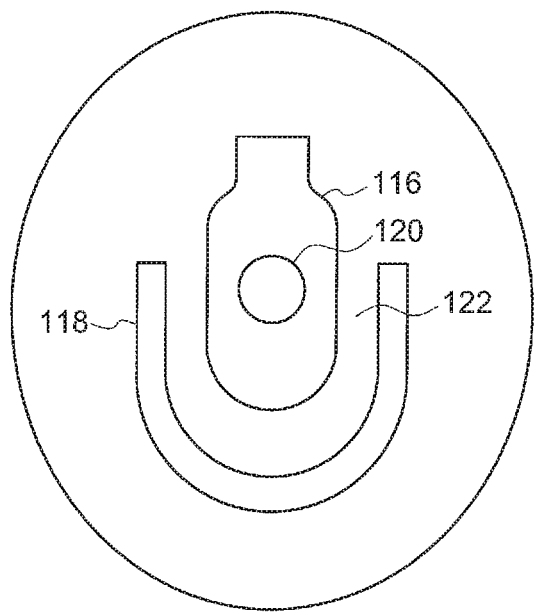
FIG. 12A is a first embodiment of the contact pad and bias ring.
Figure 12B:
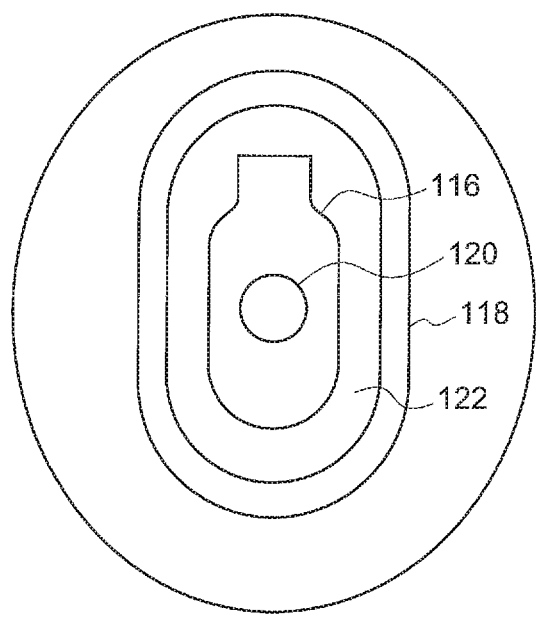
FIG. 12B is a second embodiment of the contact pad and bias ring.

FIGS. 12A and 12B illustrate two separate embodiments of the first and second contact pads 108, 110. In the first embodiment shown in FIG. 12A, the contact pad 108 includes a metallic contact 116 at least partially surrounded by a bias ring 118. In the embodiment shown in FIG. 12B, the metallic contact 116 is completely surrounded by the bias ring 118. Although two separate embodiments are shown in FIGS. 12A and 12B, it is contemplated that either embodiment could be utilized while operating within the scope of the present disclosure.

As illustrated in FIGS. 12A and 12B, each of the metallic contacts 116 includes a recessed receptacle 120 that provides a receiving location for a mating contact pin of the sensor device as will be described in detail below. The bias ring 118, whether completely surrounding the contact 116 or only partially surrounding the contact 116, is formed from an electrically conductive material. A non-conductive gap 122 is formed between the metallic contact 116 and the bias ring 118 to restrict the flow of current between the contact 116 and the bias ring 118. However, if a conductive or partially conductive material or liquid is located within the gap 122, current will be able to flow from the bias ring 118 to the contact 116, as will be described in greater detail below.

Referring now to FIGS. 10 and 11, the sensor device 2 of the present disclosure is designed to mate with the activator module 3 such that data and power can be transmitted between the two devices. In the embodiment illustrated, the connecting portion 98 includes an optical data port 124 that is formed in the generally flat face surface 126. As can be understood in the comparison between FIGS. 9 and 10, the optical data port 112 formed on the activator module 3 and the optical data port 124 formed on the sensor device 2 are designed to be physically aligned with each other such that an optical data path can be formed to transmit data to and from the sensor device 2 through the mating optical data ports.

As illustrated in FIGS. 10 and 11, the sensor device 2 includes a first contact pin 128 and a second contact pin 130. Both the first and second contact pins 128, 130 are located within and as part of a contact face surface 132 that is inclined relative to the generally planar face surface 126. A pair of side walls 134 define and support the contact face surface 132 relative to the planar face surface 126.

Figure 13:
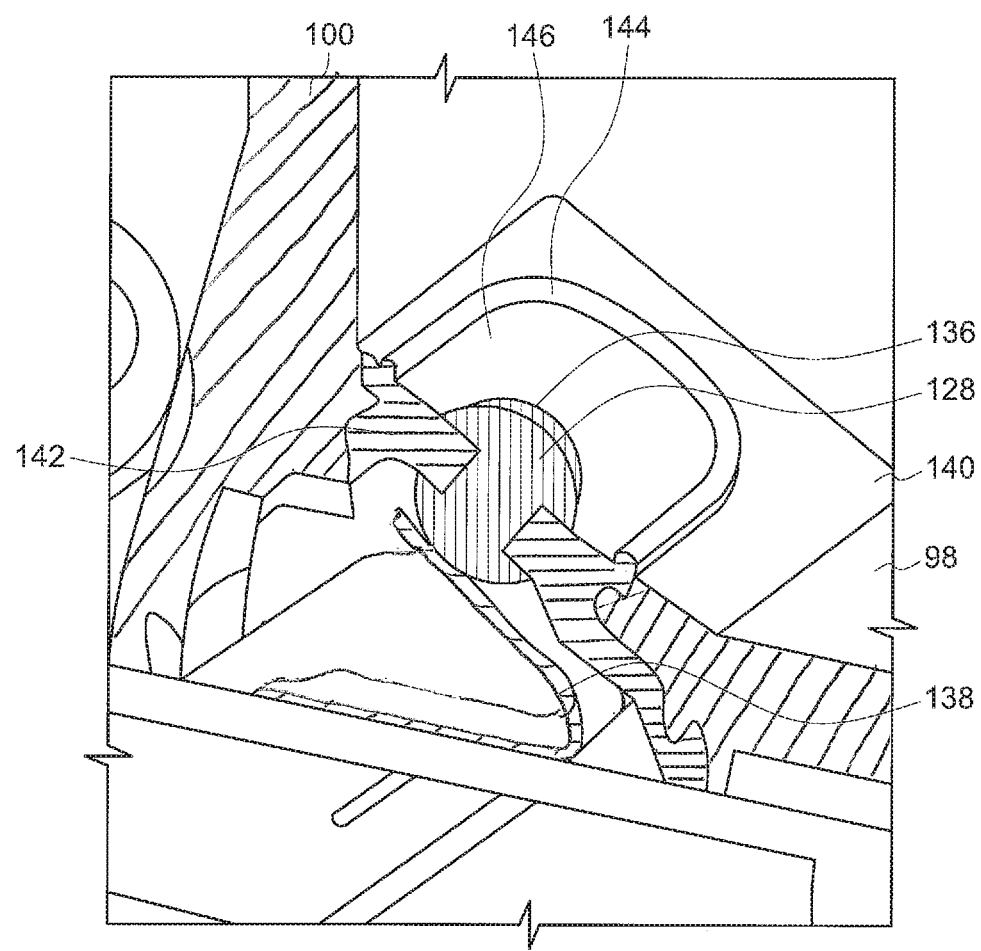
FIG. 13 is a partial section view showing the contact pin mounted within the sensor device.

Referring now to FIG. 13, each of the first and second contact pins 128 is formed from a metallic member having a domed outer surface 136. The contact pin 128 is connected to a spring arm 138 that exerts an outwardly directed physical bias force on the contact pin 128 to urge the contact pin 128 into contact with the corresponding contact pad on the activator device when the two components are mated. As can be illustrated in FIG. 13, the connecting portion 98 and the housing 100 are formed from different types of molded plastic material. Specifically, the majority of the connecting portion 98 is formed from a generally rigid plastic first material 140 while a second, more flexible plastic material 142 is used to mount the contact pin 128. The second material 142 is resilient and flexible compared to the first material 140, which allows the contact pin 128 to flex.

The second, flexible plastic material 142 forms a seal 144 that protrudes above the mounting surface 146. The mounting surface 146 surrounds and supports the contact pin 128. As illustrated, separate seals 144 surround the first contact pin 128 and the second contact pin 130. However, it is contemplated that a single, continuous seal could be used that would surround both of the contact pins 128 and 130. As can be understood in the comparisons of FIGS. 8 and 10, when the sensor device 2 mates with the activator module 3, the seals 144 surrounding each of the first and second contact pins 128, 130 engage the generally flat contact face surface 104 to provide a generally fluid-tight seal that surrounds the electrical contact between the first and second contact pins 128, 130 on the sensor device 2 and the first and second contact pads 108, 110 on the activator module 3.

Since the seal 144 surrounds the electrical contact between the contact pins 128, 130 and the contact pads 108, 110, the sealing arrangement limits the amount of debris, liquid or other elements that can affect the power transfer from the activator module to the sensor device.

Figure 14:
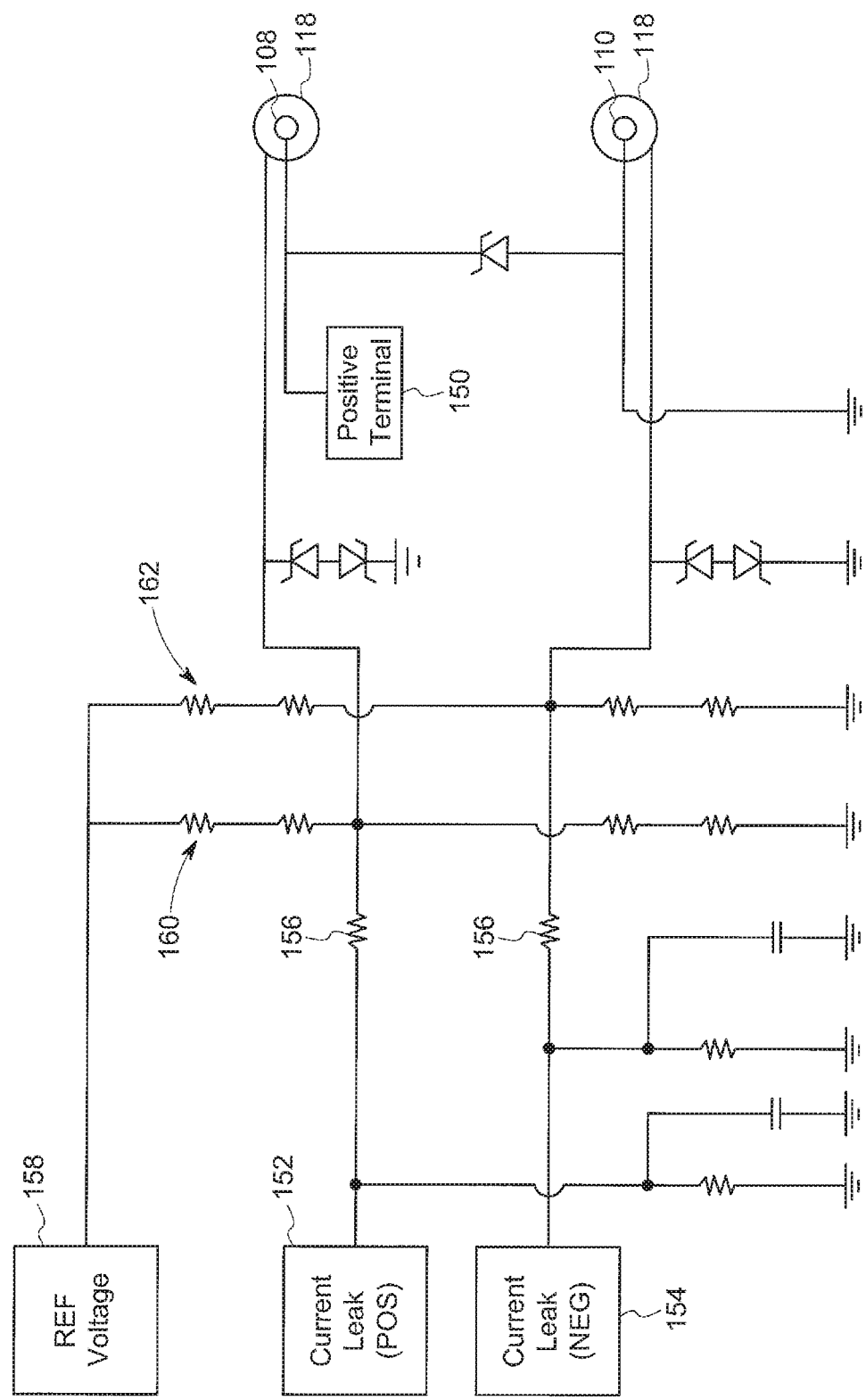
FIG. 14 is a circuit schematic showing the monitoring of the bias voltage applied to the bias rings at least partially surrounding the first and second contact pads.

FIG. 14 illustrates control circuitry that is contained within the activator module 3 to monitor for leakage current that may be generated due to a fault in the connection between the activator module 3 and the sensor device 2. As illustrated in the circuit diagram of FIG. 14, the first contact pad 108 is connected to the positive terminal 150 of the battery power supply contained within the activator module. The second contact pad 110 is connected to ground 151 such that power can be transferred from the activator module to the sensor device when the first and second contact pads 108, 110 are positioned in contact with the first and second contact pins formed as part of the sensor device. As discussed previously, a bias ring 118 surrounds or partially surrounds each of the first and second contact pads 108, 110. In the embodiment illustrated, the bias ring 118 surrounding the first contact pad 108 is connected to the current leakage detection pin 152 of the processor 26 while the second bias ring 118 surrounding the second contact pad 110 is connected to a second current leakage detection pin 154. Each of the bias rings 118 is connected to the respective current leakage pin 152, 154 through a separate current limiting resistor 156. The current limiting resistors are selected having a relatively high resistance to limit the current flowing to the respective pins 152, 154. Although the first and second bias rings 118 are shown and described as being connected to pins on the processor 26, it is contemplated that a separate detection circuit could be used, which would then communicate with the processor 26.

In the embodiment shown in FIG. 14, a reference voltage 158 generated by the processor in the activator device provides a bias voltage to both of the bias rings 118. The bias voltage to the bias ring 118 surrounding the first contact pad 108 is created by a first voltage divider 160 while the bias voltage supplied to the bias ring 118 surrounding the second contact pad 110 is generated by a second voltage divider 162. In the embodiment illustrated, both the first voltage divider 160 and the second voltage divider 162 are formed from separate resistive networks that include a series of resistors that divide the voltage reference signal 158 to create a bias voltage of approximately 1.5 volts. Although the voltage dividers 160, 162 are identical in the embodiment illustrated, it is contemplated that the voltage dividers could vary depending upon the specific requirements of the system. It is also contemplated the two voltage dividers 160, 162 could be connected to two separate control pins. In this manner, the voltage on each of the two separate control pins could be controlled separately such that the bias voltage on the two bias rings could be controlled separately. Additionally, instead of using voltage dividers, any other means of generating either a fixed or variable bias voltage level could be used as long as the impedance level at the bias ring is high enough to allow for sensing a voltage change due to leakage current and be safe in the operating environment. Additionally or alternatively, instead of sensing a voltage change due to leakage current, current sensing could also be used while operating within the scope of the present disclosure.

If a fault exists in a way that there is conductive matter touching at least one of the contact pads in a way that there is a risk of leakage current flowing out of or into the contact pad, any leakage current that exists will be detected at either one or both of the bias rings 118. These faults are most typically created when the contact surfaces get wet, either during use because of the patient sweating and the sealing is not tight or the contacts remain wet after cleaning and insufficient drying. This type of fault can lead to leakage current going from contact pad to contact pad or through the patient. Additionally, debris, hair, worn out parts could also cause such a fault, which would result in leakage current going from contact pad to contact pad.

Since both bias rings 118 are connected to the current leakage pins 152, 154, the voltage on these two bias rings 118 will be sensed and the processor 26 of the activator module 3 can either generate an alarm or interrupt the supply of power to the sensor device. Additionally or alternatively, the sensing circuit may be independent and separate from the processor 26 and operate to cut off connection to the power supply in such an error condition. It is also possible to alter the bias voltage of at least one bias ring during operation to further differentiate between various possible leakage routes (contact pad to contact pad, contact pad(s) to an external return path in an ECG electrode set, etc.). In such an embodiment, the reference voltage at each of the bias rings must be able to be adjusted separately, as described above.

Since the sensor device 2 and activator module 3 are designed to be connected and disconnected on a regular basis, the sealing arrangement and voltage detection provide two separate forms of protection against unacceptable amounts of leakage current that may be transferred to the patient. Since the monitoring circuit of FIG. 14 continuously monitors the bias voltage on the pair of bias rings, any leakage current detected at the interface between the contacts of the sensor device and the activator can be detected with the activator module.

Referring back to FIG. 1, the sensor device 2 includes an identification device 13 while the activator module 3 includes an ID receiver 18. It is contemplated that the activator module 3 can be designed including an actuation switch 164 that can be depressed by a user when the sensor device 2 is mated with the activator module 3. Upon depression of the switch 164, a handshake process begins between the sensor device 2 and the activator module 3. It is contemplated that the handshake will involve current levels under 100 µAmps and have a short duration to again protect against any unwanted current transmission to the patient. Instead of using a switch, any other mechanism indicating the possible mechanical connection of a sensor can be used, such as optical detectors, magnetic detectors or motion detectors.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of detecting a fault in the connection between an activator module and a sensor device of a two part patient monitoring device, comprising:
   providing a bias ring that at least partially surrounds a power contact pad included on the activator module;
   physically connecting the sensor device to the activator module to create the patient monitoring device, wherein a power contact pin on the sensor device engages the power contact pad and a seal member surrounds the power contact pad and the power contact pin;
   supplying power to the power contact pad;
   utilizing a processor of the activator module to monitor for a leakage current between the power contact pad and the bias ring; and
   indicating a detected fault in the connection between the activator module and the sensor device upon a detected presence of the leakage current between the power contact pad and the bias ring.

2. The method of claim 1 wherein the bias ring is physically spaced from the power contact pin by a non-conductive gap.

3. The method of claim 2 wherein the leakage current flows between the power contact pad and the bias ring upon a conductive element being present in the non-conductive gap.

4. The method of claim 1 further comprising the step of applying a bias voltage to the bias ring.

5. The method of claim 4 wherein a change in the bias voltage present at the bias ring is monitored to detect the leakage current.

6. The method of claim 4 wherein the processor of the activator module monitors the bias voltage and determines the presence of the leakage current.

7. The method of claim 6 wherein the processor monitors for a change in the bias voltage on the bias ring.

8. The method of claim 6 wherein the processor interrupts the supply of power to the power contact pad upon detection of leakage current.

9. The method of claim 6 wherein the processor generates an alarm upon detection of leakage current.

10. A method of detecting a fault in the connection between an activator module and a sensor device of a two part patient monitoring device, comprising:

providing a pair of bias rings that each at least partially surrounds one of a pair of power contact pads included on the activator module;

physically connecting the sensor device to the activator module to create the patient monitoring device, wherein a pair of power contact pins on the sensor device engages the pair of power contact pads;

supplying power to one of the pair of power contact pads;

utilizing a processor of the activator module to monitor for a leakage current between the mated power contact pads and the bias rings; and indicating a detected fault in the connection between the activator module and the sensor device upon a detected presence of the leakage current between the mated power contact pads and the bias rings.

11. The method of claim 10 wherein the sensor device includes a pair of seal members that each surrounds one of the pair of power contact pins, wherein the seal members each surround one of the pair of mated power contact pads and the power contact pins when the sensor device is connected to the activator module.

12. The method of claim 11 wherein the two power contact pads are mounted to a contact surface, wherein the seal members engage the contact surface.

13. The method of claim 10 wherein each of the bias rings is physically spaced from one of the power contact pins by a non-conductive gap.

14. The method of claim 13 wherein the leakage current flows between the power contact pad and the bias ring upon a conductive element being present in the non-conductive gap.

15. The method of claim 10 further comprising the steps of:

applying a bias voltage to each of the bias rings; and monitoring for a change in the bias voltage present at the bias rings to detect the leakage current.

16. The method of claim 15 wherein the processor in the activator module monitors the bias voltage applied to each of the bias rings.

17. The method of claim 16 wherein the processor interrupts the supply of power to the power contact pad upon detection of leakage current.

18. The method of claim 16 wherein the processor generates an alarm upon detection of leakage current.

19. The method of claim 10 wherein the sensor device includes a seal member that surrounds the pair of power contact pins, wherein the seal member surrounds the pair of mated power contact pads and power contact pins when the sensor device is connected to the activator module.

20. The method of claim 19 wherein the two power contact pads are mounted to a contact surface, wherein the seal member engages the contact surface.

* * * * *